US00PP34815P2

(12) United States Plant Patent
Fowler et al.

(10) Patent No.: US PP34,815 P2
(45) Date of Patent: Dec. 13, 2022

(54) CHERRY TREE NAMED 'HR87'

(50) Latin Name: ***Prunus avium* L.**
Varietal Denomination: 'HR87'

(71) Applicant: Hood River Cherry Company, Hood River, OR (US)

(72) Inventors: Bradley E. Fowler, Hood River, OR (US); Kathryn Klein, Hood River, OR (US)

(73) Assignee: Hood River Cherry Company, Hood River, OR (US)

( * ) Notice: Subject to any disclaimer, the term of this patent is extended or adjusted under 35 U.S.C. 154(b) by 0 days.

(21) Appl. No.: 17/349,703

(22) Filed: Jun. 16, 2021

(51) Int. Cl.
*A01H 5/12* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445
See application file for complete search history.

(56) References Cited

U.S. PATENT DOCUMENTS

PP11,392 P 5/2000 Lane

OTHER PUBLICATIONS

Tweet by Ricky C @ CherrySnobs, Jul. 22, 2018, downloaded from https://twitter.com/cherrysnobs/status/1020895504442404865?lang=en on Sep. 9, 2021, p. 1.*
The Produce Blog by Rick Chong, dated at least by Mar. 16, 2013, downloaded from www.produceblog.co/2011/11/red-striped-cherries-new-variety.html on Sep. 9, 2021, pp. 1-5.*
Sweet cherry 'Natalie(R)'—each fruit with a black stripe, downloaded from https://www.bayoz.de/en/obstsorten/susskirsche-natalie/ on Sep. 9, 2021, p. 1-2.*
The Striped Cherry of Paris—Andreas, downloaded from ttps://www.andreasveg.co.uk/products/the-striped-cherry-of-france on Sep. 8, 2021, p. 1-2.*
"Sweet Cherries with Dark Stripe", Alex Zorach, Jul. 25, 2011, downloaded from https://cazort.net/photos/sweet-cherries-with-stripe.*

* cited by examiner

*Primary Examiner* — Anne Marie Grunberg
(74) *Attorney, Agent, or Firm* — Randall Danskin, P.S.

(57) ABSTRACT

As a mutation of the cherry tree variety 'Lapins', a new and distinct variety of cherry tree, which is denominated varietally as 'HR87', is described with variable, but typically bright red, sometimes blonde areas of skin, sometimes darker areas of skin, of the fruits and a consistent, notable, dark red line associated with the suture of each fruit under the ecological conditions prevailing in the Hood River Valley of Oreg., USA. The distinct color variation of the sometimes bicolored fruit has a variable (fruit to fruit) pattern of red pigmentation over a sometimes blonde background. The fruits are distinguished by a consistent dark red line of pigmented cells along the suture line of the fruit. This dark red line consistently persists through the variable colored flesh to the pit of the fruit.

10 Drawing Sheets

Latin name: *Prunus avium* L.

Variety denomination: The invention relates to a new, novel, and distinct variety of cherry tree, a *Prunus avium* L., with a variety denomination hereinafter as 'HR87'.

SUMMARY

The new variety 'HR87' is believed to be a chimera of the cherry variety known as 'Lapins', an unpatented variety of cherry bred and released by Agriculture Canada Research Station, Summerland, British Columbia, Canada. The chimera was discovered in 2008 in a 'Lapins' cherry orchard owned by the applicant in the Hood River Valley of Oreg., USA.

Unusual cherries were discovered while packing fruit harvested from the aforementioned 'Lapins' orchard. The unusual cherries, while similar in size and shape to 'Lapins' fruits, exhibited a distinct bright red and blonde coloration and a notable, consistent, dark red line on the suture of the fruit. The pigmented areas of the fruit were irregular, sometimes affecting the skin only, but also at times penetrating deeper into the typically blonde flesh, and sometimes all the way to the pit. After noting the unusual cherries during packing a second year, an active search was made prior to harvest in the third year to discover which tree was producing the unusual fruit. The fruit was discovered to occur on one branch of an otherwise normal 'Lapins' tree. The variety was characterized as a bud mutation of 'Lapins'.

Steps were taken to test the selection further and to preserve the new variety. Scions of the new variety were placed on 12 cherry rootstocks in 2010 to determine if the distinctive fruit characteristics were transferred to succeeding generations. In 2015, a subsequent third generation was propagated with approximately 500 trees in multiple Hood River Valley locations on land owned by the applicant. All trees of succeeding generations yielded fruit with the characteristics herein described.

In other particulars, the new variety is similar to its parent 'Lapins' except that the flavor may be described as somewhat more mild. The fruit shape, size, texture, firmness, and harvest maturity date are similar to the parent. The overall tree characteristics, such as, leaf size, shape, and color, bloom size and structure, bloom date, as well as tree size, growth, and structure are similar to the 'Lapins' parent.

Continued observations of the original chimera branch and its progeny derived by budding propagation occurred along with fruit quality testing of second and third generation fruits. The observations and testing established that the distinctive coloration of the fruit was consistent and of sufficient merit to justify naming the selection and securing plant patent protection of the variety.

Following is a detailed description of the 'HR87' variety of cherry tree. Such description is based on observations and with reference to botanical authorities.

BRIEF DESCRIPTION OF THE DRAWINGS

The accompanying drawings are color photographs of the new cherry tree variety under the ecological conditions prevailing in the Hood River Valley of Oreg., USA.

FIG. 7 is a color photograph showing 'HR87' bloom color, structure, and size relative to photographer's hand.

FIG. 8 is a color photograph showing 'HR87' bark color, lenticels, outfacing to downward bloom orientation, and branch angle orientation.

FIG. 9 is a color photograph showing 'HR87' newly expanding leaves.

FIG. 10 is a color photograph showing 'HR87' characteristic upright, yet spreading structure. This general tree shape and structure is maintained as the tree grows and develops in subsequent years. Slight anthocyanin in growing shoot tips is also depicted.

Figure 1:
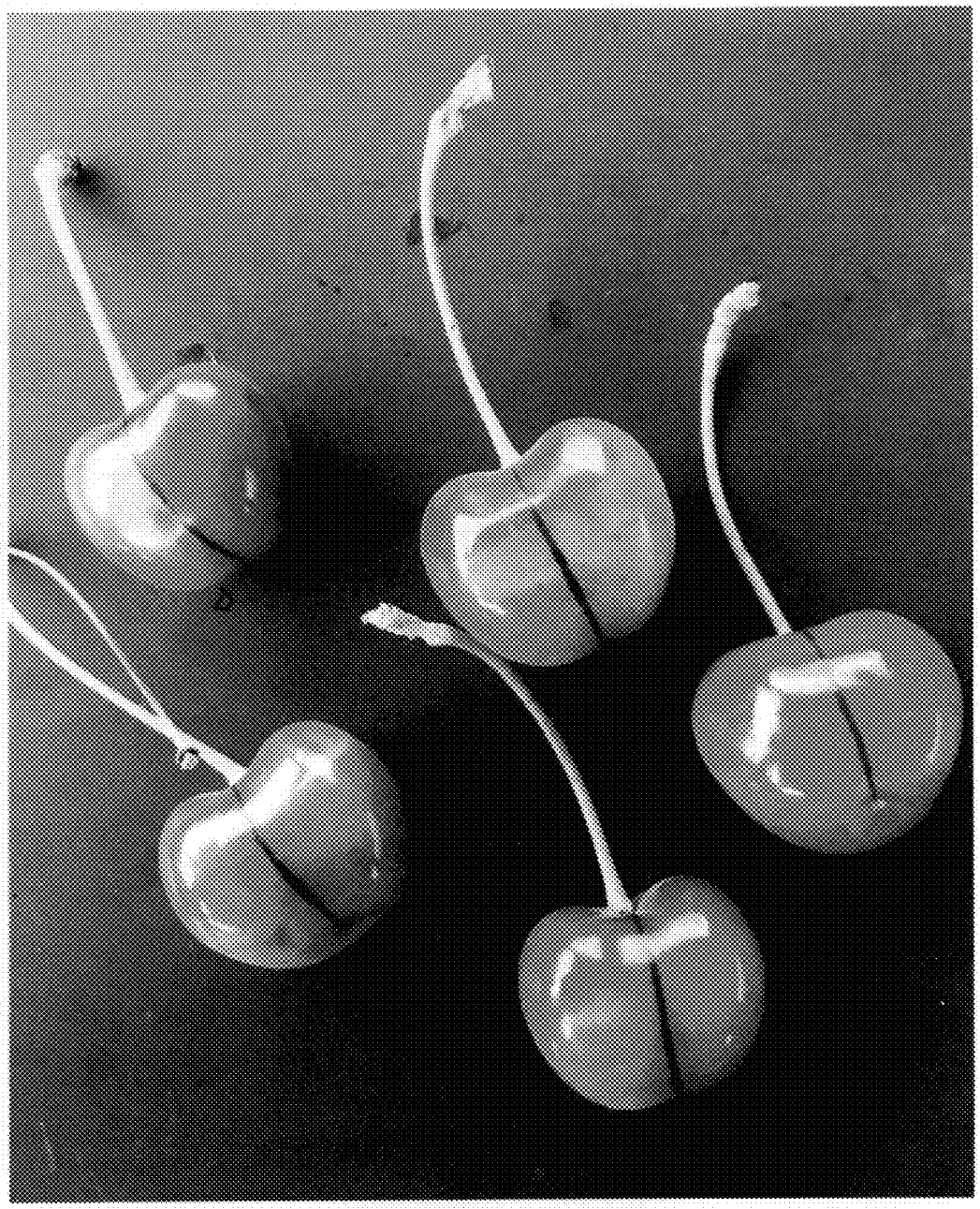
FIG. 1 is a color photograph showing the 'HR87' fruit 7 days prior to maturity. Blonde areas on the skin tend to fill in to a bright red at maturity, while the dark red line at the suture remains.
Figure 2:
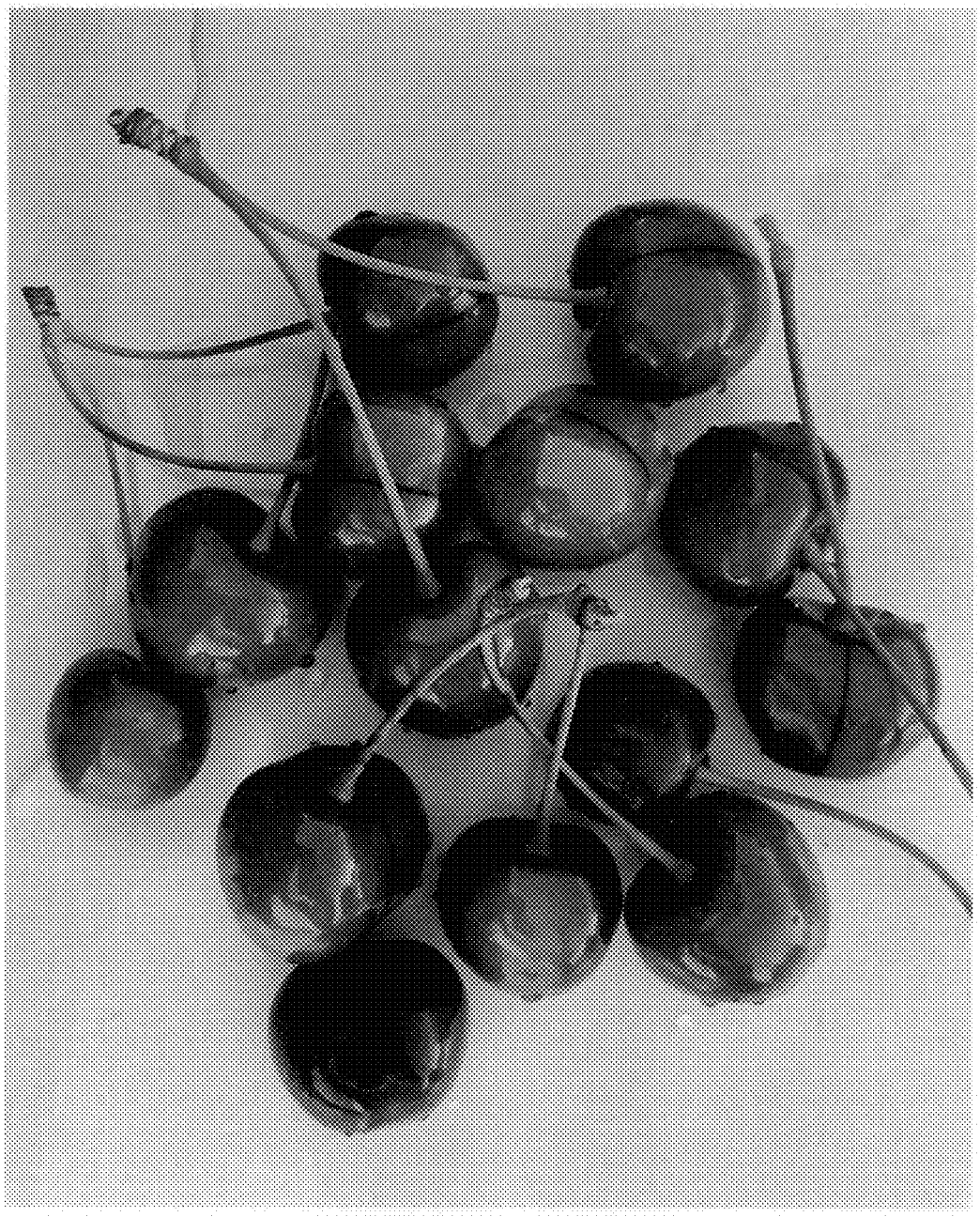
FIG. 2 is a color photograph showing the 'HR87' fruit at maturity with mostly bright red skin (some mottling) and dark red suture line.
Figure 3:
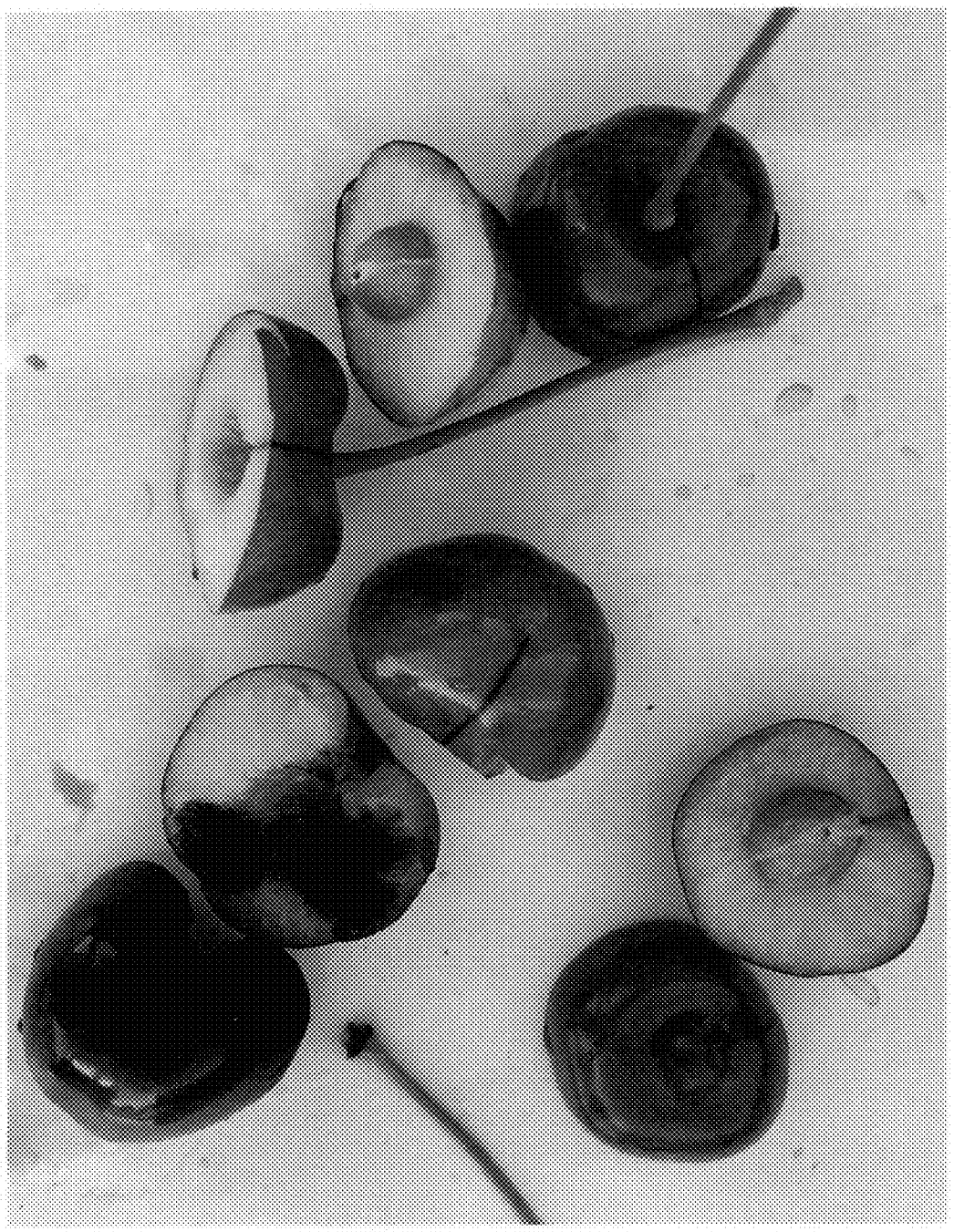
FIG. 3 is a color photograph showing the 'HR87' fruit at maturity. The sections show mostly blonde flesh with occasional dark mottling. A consistent red line on the suture extends to the pit.
Figure 4:
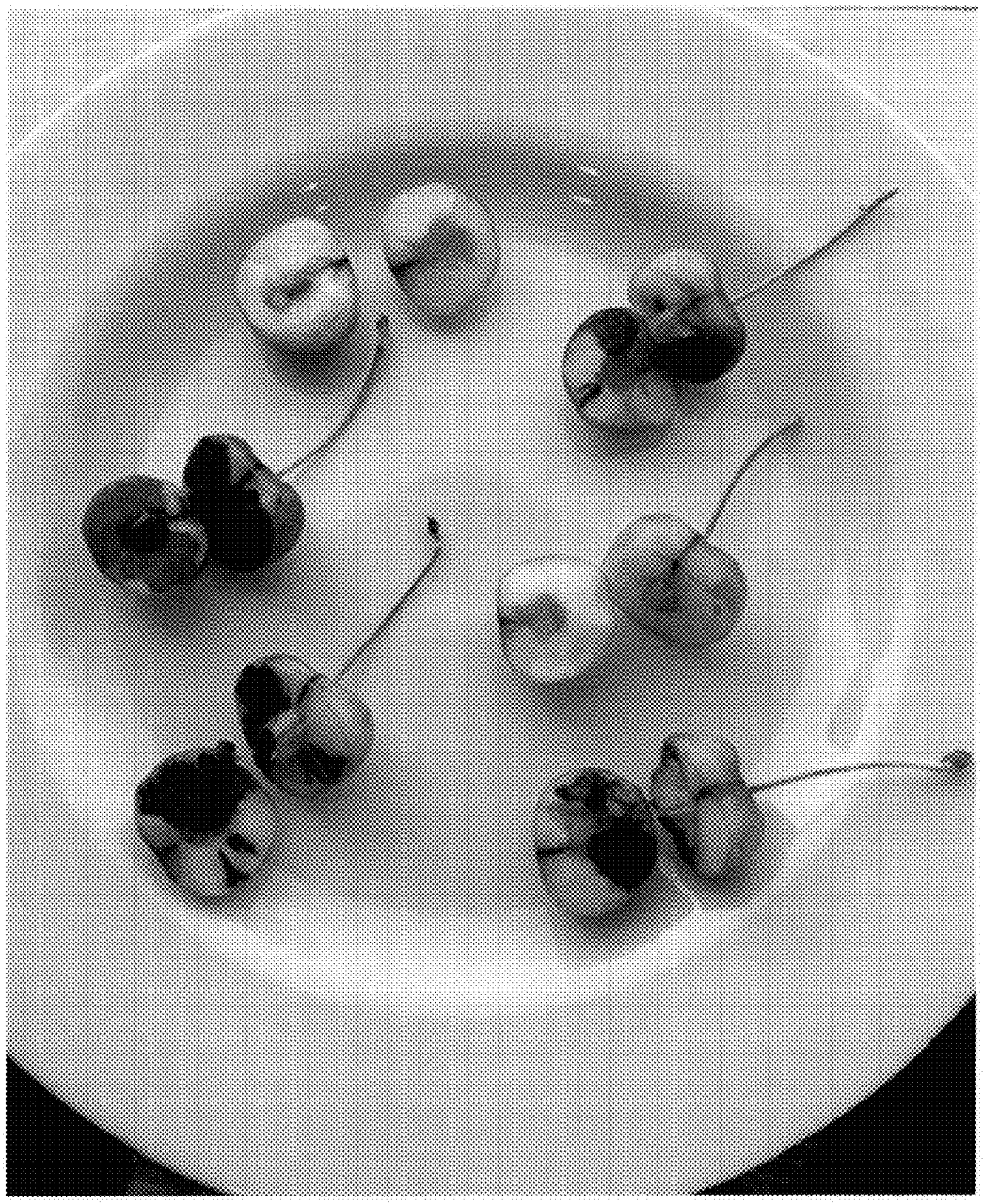
FIG. 4 is a color photograph showing variance similar to FIG. 3 among the flesh of the 'HR87' fruit.
Figure 5:
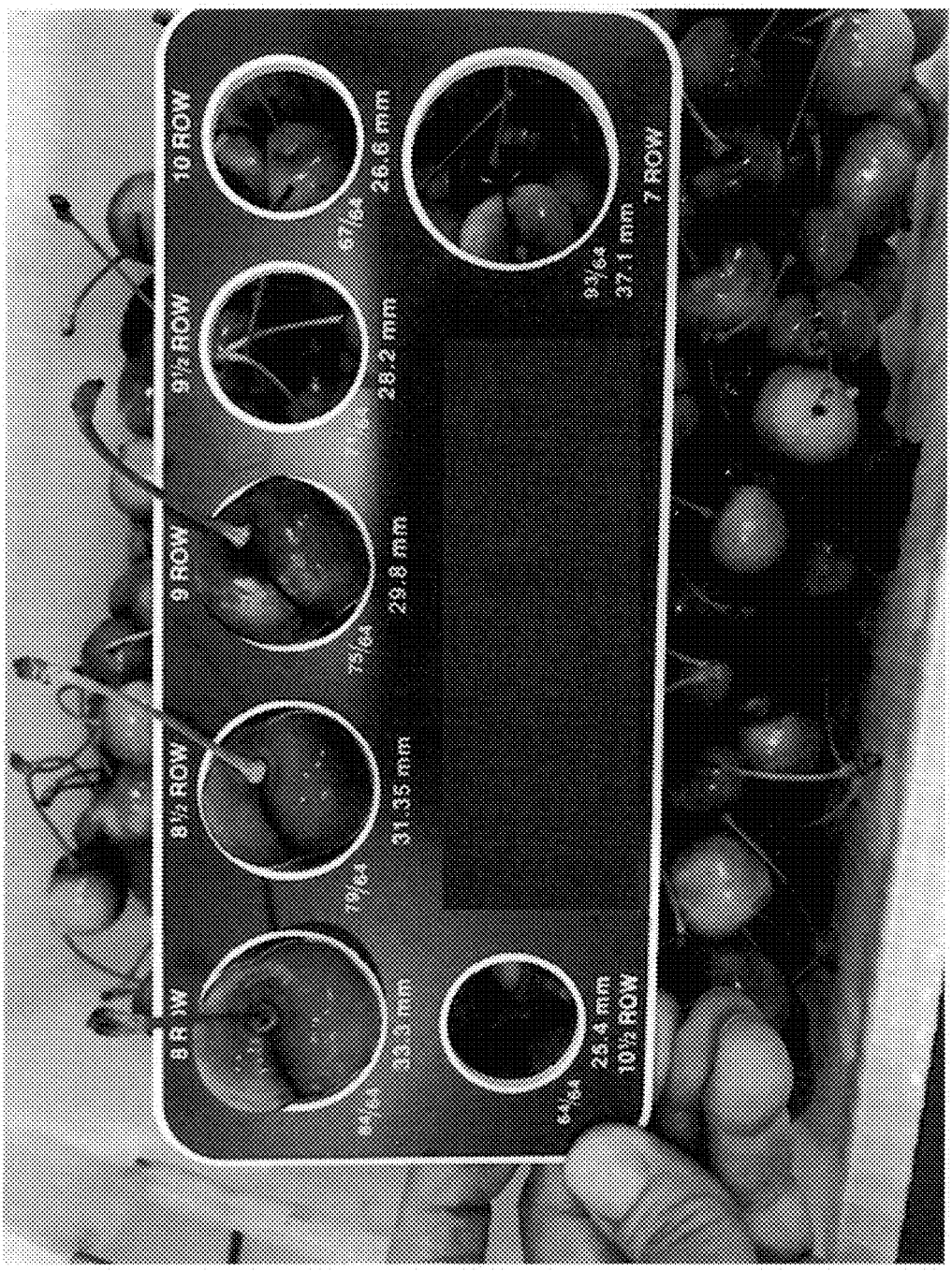
FIG. 5 is a color photograph showing the size distribution of 'HR87' fruit harvested Aug. 7, 2019 from progeny of the original chimera branch.
Figure 6:
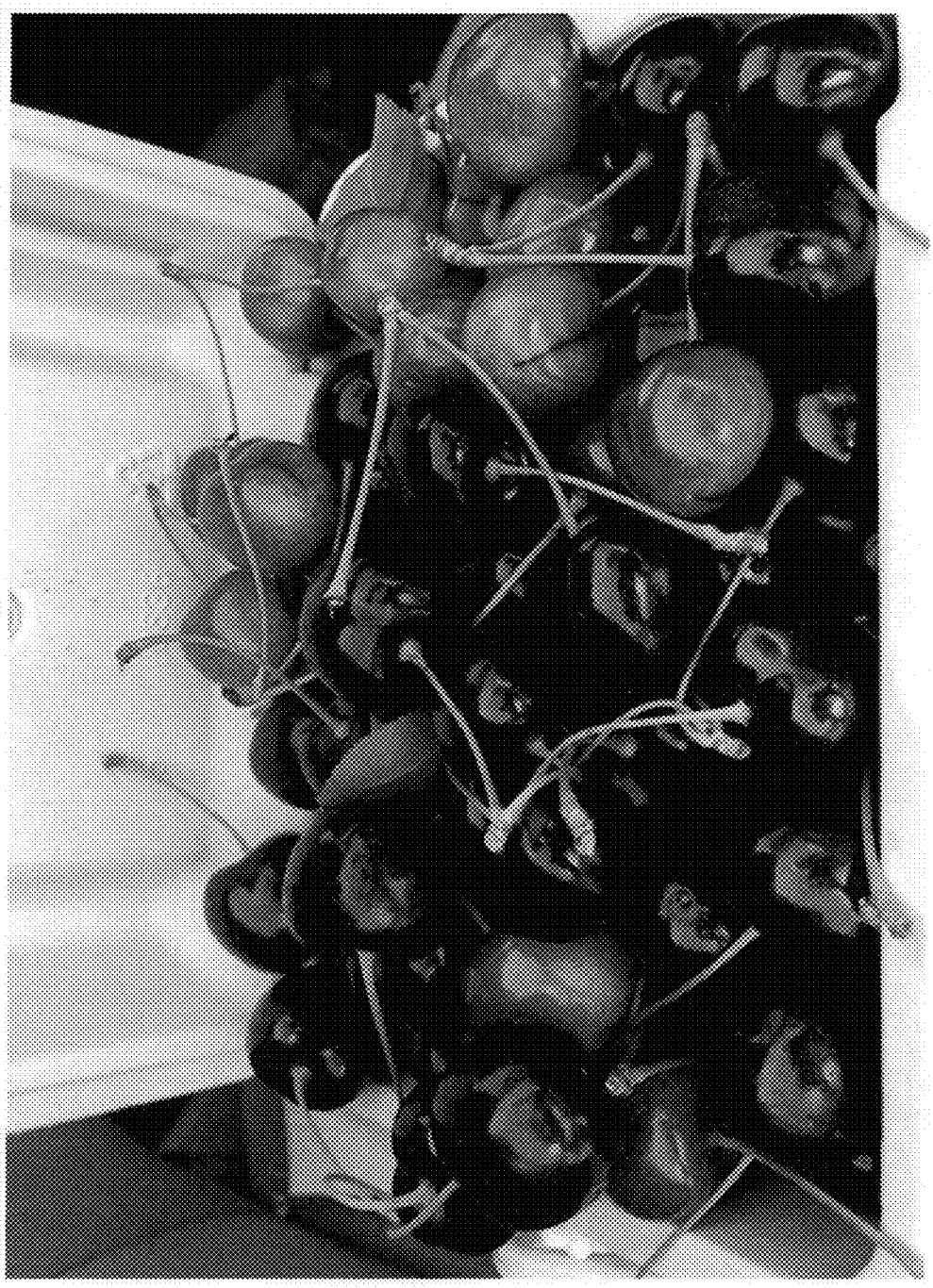
FIG. 6 is a color photograph showing darker-colored fruit harvested Aug. 7, 2019 from a 'Lapins' tree and lighter-colored fruit harvested the same day from the same 'Lapins' tree, but from the chimera that yielded the 'HR87' variety.
Figure 7:
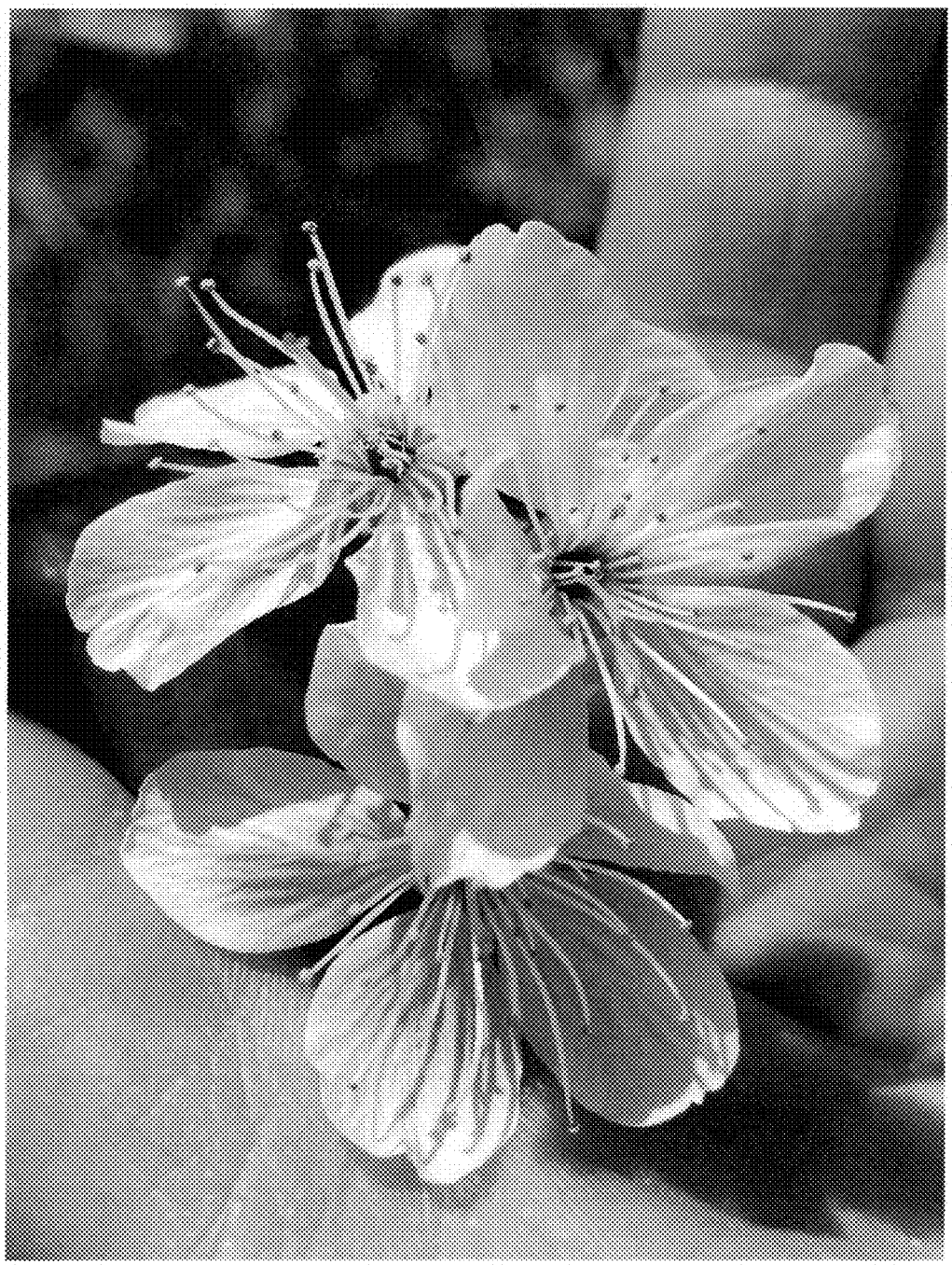
FIGS. 7-10 show an 'HR87' tree at the beginning of the third year after transplanting.
Figure 8:
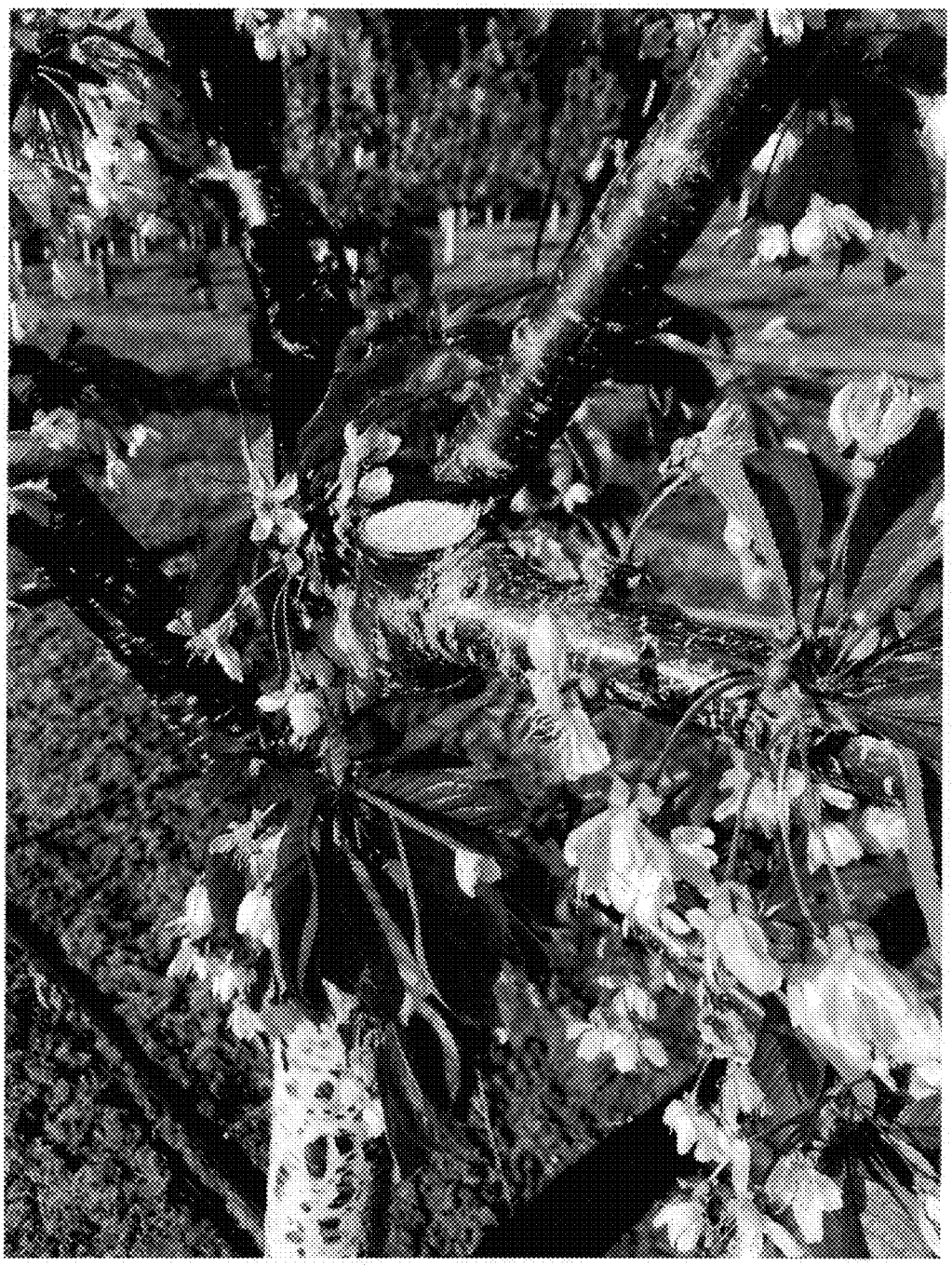
Figure 9:
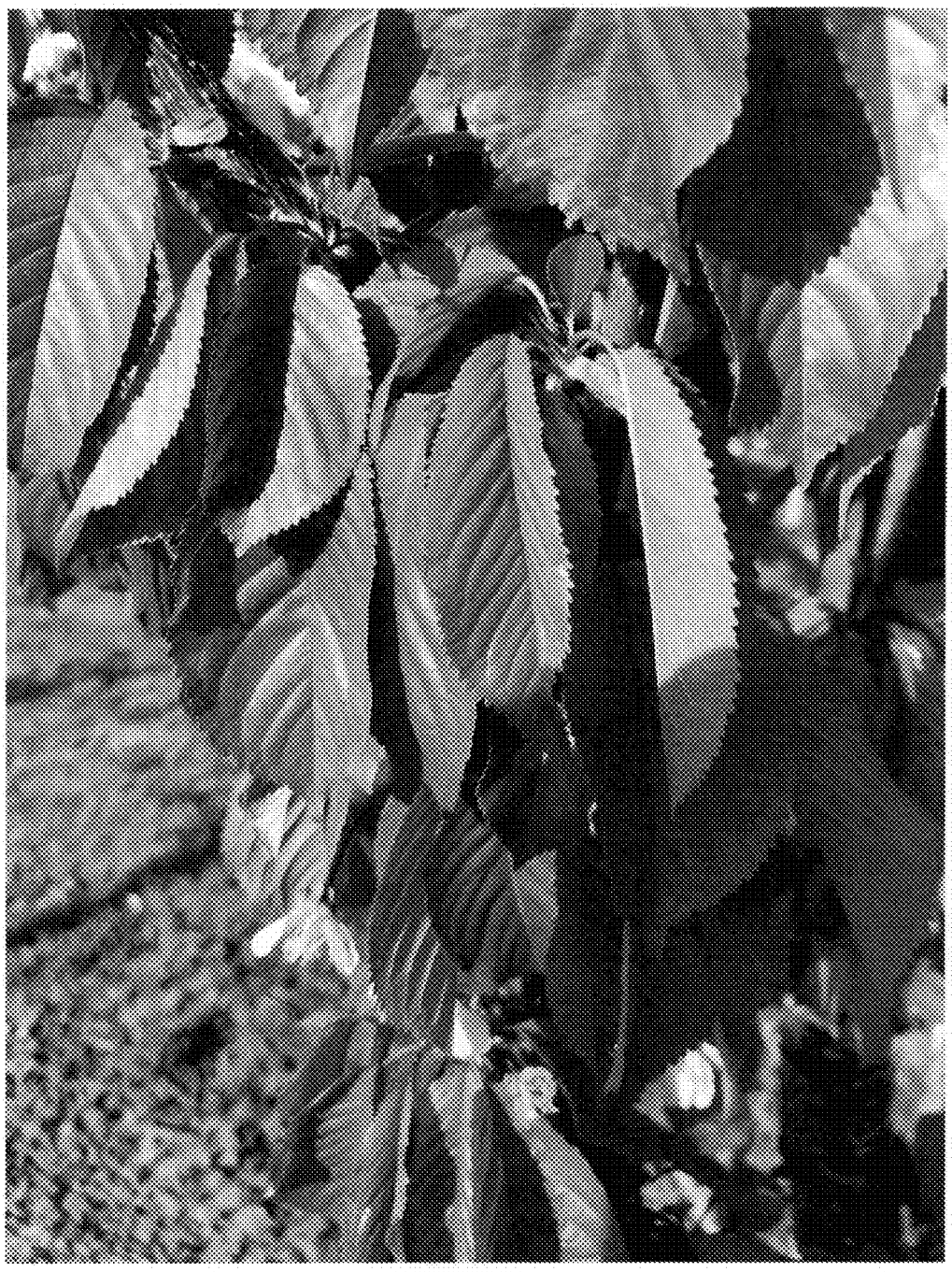
Figure 10:
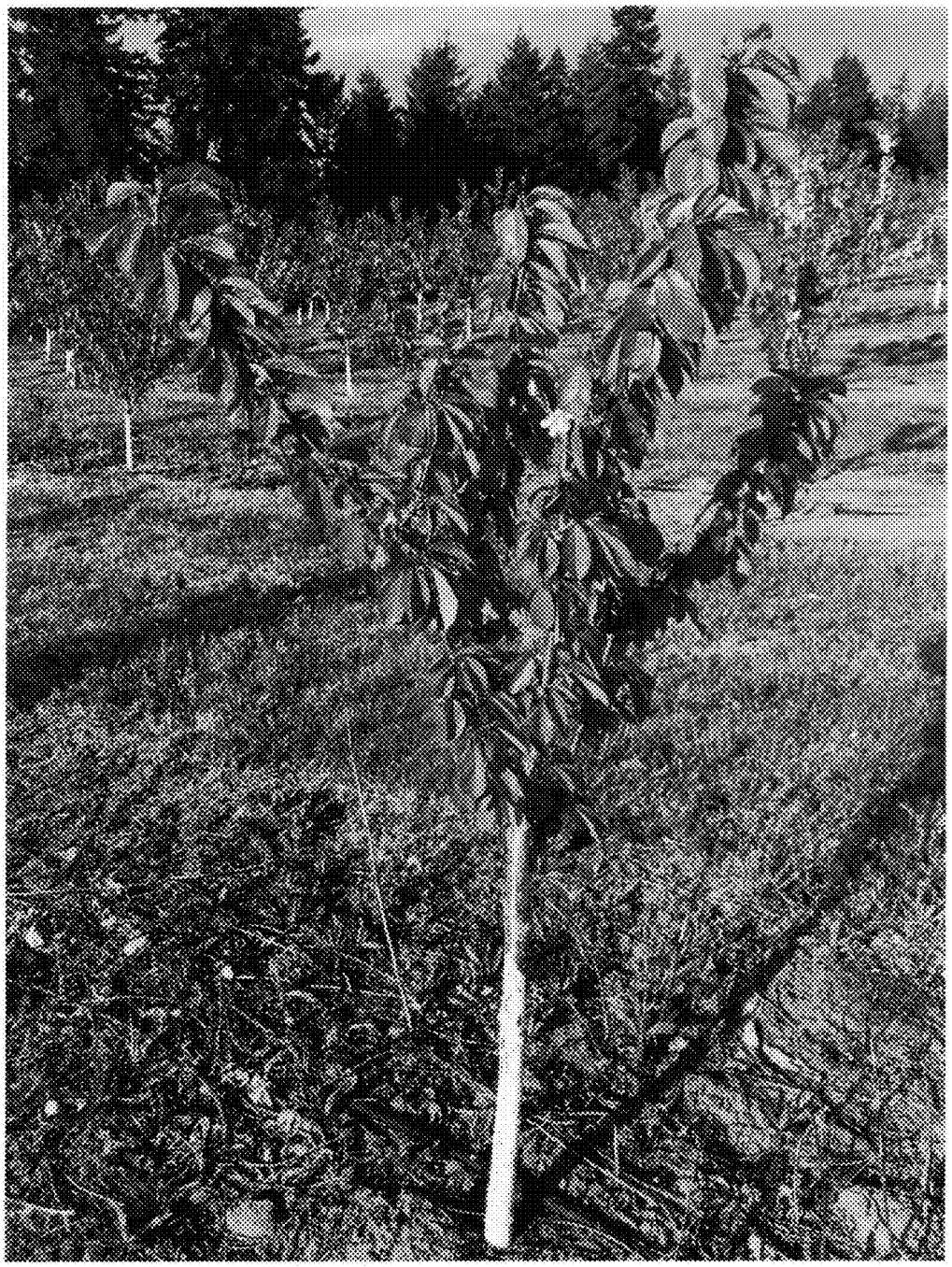

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Fifth Edition (2007), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of cherry tree, the following has been observed during the year 2019 under the ecological conditions prevailing at the grower's property, which is located at 700 feet elevation in the Hood River Valley of Oreg., USA. Some of the description is referenced to the "parent 'Lapins'" grown on the same property as the new variety and, thus, subject to the same ecological conditions.

Tree: General.

*Size*.—Medium to large. Trunk size for 4-year old transplant 40 centimeters (cm) above soil level: 9 cm±2 cm.

*Vigor*.—High, similar to parent 'Lapins'.

*Form*.—Upright, spreading.

*Growth*.—Moderate.

*Hardiness*.—Not directly measured, but expected to be the same as parent 'Lapins', which is considered hardy compared to other varieties.

*Production*.—Not directly measured, but expected to be the same as parent 'Lapins', which is considered very productive compared to other varieties.

*Bearing*.—Mid-late season maturity. Same as parent 'Lapins'; about 8 days after Bing (unpatented).

Tree: Trunk.

*Form*.—Straight.

*Size*.—Tree size for 4-year old transplant: less than 6 meters high and 4 meters wide on seedling root.

*Texture*.—Medium, smooth.

*Color*.—RHS Medium Brown Group 166A (four year-old tree).

Tree: Branches.

*Main branches*.—Upright, spreading, thick, strong with distinct lenticels.

*Lateral branches*.—Upright, spreading, smooth with distinct lenticels.

*Branchlets*.—Glabrous areas, reddish brown with dull grayish areas.

*Bark coloration*.—Mature branch — RHS Medium Brown Group 165A. One-year old wood — RHS Yellow Brown Group 165B.

*Lenticels* (*one-year old wood*).—About 1 per square centimeter (cm), irregularly spaced. Color — RHS Light Yellow Brown Group 165D.

*Bud burst*.—Early to mid timing, approximately April 1 under the ecological conditions prevailing at the grower's property (similar to parent 'Lapins').

Leaves.

*Leaf buds*.—Narrow, pointed, slightly out-facing; RHS Yellow Brown Group 167D.

*Vegetative bud shape of apex*.—Acute.

*Vegetative bud size*.—Length 9 mm±1 mm; width 2.6 mm±0.2 mm.

*Position of vegetative bud in relation to one-year-old shoot*.—Buds held slightly out.

*Leafing date.*—Approximately April 21 under the ecological conditions prevailing at the grower's property.

*Anthocyanin color in the apex of young shoots.*—Slight anthocyanin.

*Size of vegetative support.*—Diameter at base of one-year old shoot 11 mm±2 mm.

*Degree of feathering.*—One-year-old shoots rarely feathered.

*Pubescence description.*—Very little pubescence on young shoot apex.

*Leaf size.*—Large, green length: 4-8 inches, width: 2-4 inches (with good husbandry).

*Leaf color upper side.*—RHS Brown Green Group 147A.

*Leaf color lower side.*—RHS Brown Green Group 147B.

*Venation color.*—Upper and lower side veins RHS Light Yellow Brown Group 162B (upper veins very fine approximately 0.5 mm wide).

*Leaf blade pubescence.*—Fine pubescence along veins on lower leaf side.

*Form.*—Elliptical with broader base.

*Apex.*—Taper pointed.

*Leaf blade length of tip.*—Approximately 10 millimeters (mm)±5 mm.

*Margin.*—Dentate.

*Degree of indentation.*—Medium; 3 indentations/cm of leaf margin; 2 mm±0.5 mm deep.

*Petiole groove.*—On entire upper side; 0.5 to 1.0 mm deep; approximately 0.5 mm wide.

*Petiole color.*—Upper side RHS Dark Purple Red Group 059A; lower side RHS Light Yellow Brown Group 162B.

*Position of nectaries on leaf.*—Predominantly on petiole, 0 to 10 mm below leaf blade.

*Nectaries on shoot leaves.*—Mostly 2 nectaries per leaf; 2.5 mm±0.5 mm long, 1.5 mm±0.2 mm wide; oval to kidney shape; RHS Light Yellow Brown Group 159A.

*Nectaries on spur leaves.*—0 to 2 nectaries per leaf; 1.5 mm±0.5 mm long, 0.75 mm±0.2 mm wide; oval to round shape; RHS Light Yellow Brown Group 159A.

*Length of one-year-old internode.*—3.5 cm±1.0 cm.

Flowers:

*Bloom period.*—Early to mid timing, 2 days ahead of 'Bing' (unpatented), first bloom approximately April 7 and full bloom approximately April 13 under the ecological conditions prevailing at the grower's property.

*Flower buds.*—Round, somewhat outward facing; RHS Yellow Brown Group 167D.

*Flowers per bud.*—2-5, mostly 3-4.

*Duration of bloom period.*—6-10 days.

*Flower density.*—Medium to heavy.

*Flower appearance.*—In clusters, dense on spurred wood.

*Flower type.*—Single.

*Flower diameter.*—42 mm±5 mm.

*Fertility.*—Self-fertile.

*Flower buds.*—Large, round, slightly elongated.

*Petal size.*—Mean 22 millimeters (mm).

*Petal shape.*—Elliptical.

*Petal position of margins.*—Slightly overlapping.

*Petal color.*—RHS White Group 155D.

*Stigma position.*—Stigma position at floral center surrounded by anthers with petals distal to stigma.

*Anther position.*—Petals surround anthers.

*Floral organs color.*—Anther filaments — RHS White Group 155D. Pollen — RHS Light Yellow Brown Group 163D. Style — RHS Yellow Green Group 154C. Stigma — RHS Green Brown Group 153B.

Fruit:

*Pedicel.*—Length 5-7 cm; RHS Yellow Green Group 154C.

*Maturity date.*—8-10 days after 'Bing' (unpatented).

*Fruit shape.*—Top view — oval, slightly flat on suture side; Side view — suture side, broader than tall with medium shoulders; End view — rounded.

*Suture.*—Slightly flattened, distinct line on suture; RHS Dark Violet Group N 079B.

*Fruit apex.*—Flat, slight depression in bowl.

*Skin color.*—Variable; 85% RHS Red Group 045B; 10% RHS Orange Group 024C; 5% mottled RHS Purple Group 064B.

*Bloom.*—Fruit finish is shiny, bloom lacking.

*Fruit lenticels.*—Approximately 50 lenticels/$cm^2$, 0.5 mm diameter, slightly more red pigment (RHS Red Group 045B) than surrounding skin.

*Flesh color.*—Variable; 95% RHS Orange Group 025D; 5% RHS Purple Group 059C.

*Fruit diameter.*—26.1±2.0 mm.

*Firmness.*—Average 358 (Firmtech) (With 30 ppm Gibberellic acid application).

*Titratable acidity.*—Average 508 milligrams per 100 milliliters juice.

*Soluble solids.*—Average 24.8%.

*Fruit taste.*—Sweet, somewhat mild.

*Juiciness.*—Moderate to very juicy; 38% juice by weight, including pit.

*Fruit juice color.*—Very light colored RHS Light Yellow Orange Group 011D. If mottling of flesh is present, then juice is darkened to the degree of mottling toward RHS Purple Group N 079C.

*Adherence of flesh to stone.*—Semi-adherent.

*Stone size.*—Large relative to fruit size.

*Stone shape.*—Round.

*Stone size.*—10.8 mm±1 mm.

*Stone color.*—RHS Yellow Orange Group 016A if stone is moist.

*Stalk.*—Length 4.5 cm±1 cm; width 1.8 mm±0.2 mm; color RHS Yellow Green Group 154C.

*Abscission layer.*—Fruit well-attached at normal harvest maturity; abscission layer develops as fruit passes normal maturity.

*Fruit set.*—High.

*Market class.*—Sweet dessert.

*Chilling required.*—400 to 500 chilling hours; same as parent 'Lapins'.

Although the new variety of cherry tree possesses the described characteristics when grown under the ecological conditions prevailing in the Hood River Valley of Oreg., USA, it should be understood that variations are to be expected in the usual magnitude and characteristics incident to changes in growing conditions, fertilization, pruning, pest control, frost, climatic variables, and horticultural management.

Having thus described and illustrated a new variety of cherry tree, what is claimed to secure a plant Letters Patent is:

1. A new and distinct variety of cherry tree, substantially as illustrated and described, which is characterized principally as to novelty by variable, but typically bright red, sometimes blonde areas of skin, sometimes darker areas of skin, of the fruits and a consistent, notable, dark red line associated with the suture of each fruit under the ecological conditions prevailing in the Hood River Valley of Oreg., USA.

* * * * *